United States Patent [19]

Hielscher et al.

[11] Patent Number: 5,403,452
[45] Date of Patent: Apr. 4, 1995

[54] METHOD FOR DETERMINING GAS CONCENTRATIONS AND GAS SENSOR WITH A SOLID ELECTROLYTE

[75] Inventors: Bernd Hielscher, Bad Vilbel; Berthold Horn, Friedricksdorf; Martin Schmäh, Frankfurt, all of Germany

[73] Assignee: Hartmann & Braun, Frankfurt, Germany

[21] Appl. No.: 930,552

[22] PCT Filed: Apr. 17, 1991

[86] PCT No.: PCT/DE91/00313
§ 371 Date: Sep. 28, 1992
§ 102(e) Date: Sep. 28, 1992

[87] PCT Pub. No.: WO91/16624
PCT Pub. Date: Oct. 31, 1991

[30] Foreign Application Priority Data
Apr. 26, 1990 [DE] Germany ............ 40 13 382.6

[51] Int. Cl.⁶ ............................................. G01N 27/26
[52] U.S. Cl. .......................... 204/153.18; 204/153.14; 204/153.16; 204/412; 204/425; 204/426; 204/428
[58] Field of Search .............. 204/412, 415, 421, 424, 204/426, 427, 428, 425, 153.14, 153.16, 153.18

[56] References Cited
U.S. PATENT DOCUMENTS

| 4,227,984 | 10/1980 | Dempsey et al. | 204/412 |
| 4,269,684 | 5/1981 | Zick | 204/406 |
| 4,400,260 | 8/1983 | Stahl et al. | 204/412 |
| 4,820,386 | 4/1989 | La Conti et al. | 204/153.18 |
| 4,900,425 | 2/1990 | Sasayama et al. | 204/426 |
| 5,215,643 | 6/1993 | Kusanagi et al. | 204/426 |

Primary Examiner—John Niebling
Assistant Examiner—Bruce F. Bell

[57] ABSTRACT

The invention relates to a method for determining the concentration of gases in a mixture of gasses by means of a gas sensor composed of three electrodes 1,2,3 and a solid electrolyte 4 upon the surface of which are secured the electrodes. A voltage Us being composed of a dc component Udc and an ac component Uac is applied to at least two electrodes, the measuring electrode 1 and the counter electrode 2. Us is controlled with reference to the reference electrode 3. The voltage components Udc and Uac of the voltage Us are chosen so that the metal salt formed by the ions of the solid electrolyte 4 with the gaseous components to be detected is again decomposed. The ion current flowing between the electrodes is measured in dependence upon the voltage as applied. The concentration of the several gasses can be determined by known mathematical methods from the functional relation between the ion current and the voltage Us.

19 Claims, 2 Drawing Sheets

METHOD FOR DETERMINING GAS CONCENTRATIONS AND GAS SENSOR WITH A SOLID ELECTROLYTE

BACKGROUND OF THE INVENTION

The present invention relates to a method and an apparatus for determining the concentration of gases in a mixture of gases by means of a gas sensor having a solid electrolyte.

A plurality of embodiments of electrochemical gas sensors is based on watery electrolytes or polymeric solid electrolytes (U.S. Pat. No. 4,227,984). The materials as per the latter are water containing proton conductors.

The use of a watery or water containing electrolyte limits severely the field of use for the sensors. Because the water in the electrolyte evaporates even at temperatures below 100° C. and the, conductivity of the electrolyte drops sharply.

Another drawback of these gas sensors using a water containing electrolyte is the considerable expenditure needed for miniaturization and realization of a compact design ( British patent application 22 28 327).

The measuring effect of such sensors is based on the electrochemical oxidation or reduction of the gas component to be detected and on the formation of protons or water at a measuring or a counter electrode. The selectivity of these sensors is thus limited by the oxidation or the reduction potential of the gas species to be detected.

It is known that the concentrations of gases in a mixture can be measured by means of ion-conductive materials provided certain conditions are met ( see H. Rickerr "solid ion conductors principles and application" in a journal titled Angew. Chem. (applied chemistry) vol. 90 pages 38–48, 1978). For that purpose a galvanic chain is constructed being comprised of two electrodes and a solid electrolyte wherein one electrode, the so called measuring electrode, is exposed to the gas whose composition is unknown and the other electrode is held to constant conditions through appropriate features. In order to obtain a suitable measuring signal essentially two measuring principles are used:

a) measuring the voltage between the electrodes (potentiometer measurement) without any current flow if at all possible or b) measuring the current between the electrodes at a given voltage (potentiostatic or amperic measurement)

A known example for the principle a) is the lambda probe using zirconium dioxide $ZrO_2$ as solid electrolyte. This probe is used for measuring the concentration of oxygen. The counter electrode is exposed to the relatively constant partial pressure of oxygen in air.

Such measurements can also be conducted when the solid electrolyte cannot directly transmit the ions of the gas to be detected (German patent 29 26 172 C2). Furthermore it is not always necessary to expose the counter electrode to a reference gas, but the latter electrode may be comprised of a material which contains the ions of the solid electrolyte either as a chemical compound or in elemental form. The partial gas pressure is determined by means of such a galvanic chain and uses the chemical reaction of the gas to be detected with an electric-active ion of the solid electrolyte. For this an electric voltage (EMF) is measured between the reference and the measuring electrodes, a reaction takes place at the latter. The higher the partial pressure of the gas reacting with the ion the larger is the electric voltage.

The dependency of the partial pressure is determined by the Nernst equation:

$$EMF = E_0 + (R*T)/(n*F) * \text{lognat}(p_{gas}) + E_r + Z$$

Herein,

R is the universal gas constant
T is the absolute temperature
F is the Faraday constant
n is the number of electrons that are transferred
Pgas is the partial pressure of the gas to be measured.

The parameter $E_r$ contains the portion of the counter electrode that is independent from the partial pressure. and the parameter Z combines all terms that are attributable to other gas components. The quantity $E_0$ contains the Gibbs reaction enthalpy to be calculated for the reaction of the gas with the ions of the solid electrolyte by means of the equation $G/(n*F) = -E_0$.

The quantity G informs about the thermodynamic stability of a compound. The ions of the solid electrolyte may combine with different gases in differently stabile compositions.

For example, sodium ions can be transferred through the solid electrolyte Na-$\beta$-alumina and together with sulfur-dioxide in the presence of oxygen it will form sodium sulfate or together with carbon-dioxide it will form sodium carbonate. In the most simple case the compound with the largest reaction enthalpy will form under conditions given by the gas mixture, in the present example this is the case for sodium sulfate.

FIG. 1 illustrates the temperature dependency of the EMF in principle and as determined by the Nernst equation for the formation of the metal salts sodium carbonate $Na_2CO_3$ and sodium nitrate $NaNO_3$. Herein the upper curve illustrates in each instance the situation for a high partial pressure and the lower curve represents the EMF for a low partial pressure of $CO_2$ and $NO_2$. Thus, there exists a temperature range and a partial pressure range wherein an EMF is produced by a Na chain and for a particular partial pressure with which a particular $CO_2$ partial pressure can be associated.

A separate potentiometric determination of partial gas pressure of either $NO_2$ or $CO_2$, both gases being present, by means of a Na chain is thus possible only under very limited conditions. The thermodynamic calculations for other metal salts such as Ag salts establish likewise temperature and partial pressure ranges in which several reactions run in parallel in a competing fashion because their reaction enthalpy and EMF values are identical. Consequently the EMF measurement is inconclusive as to the partial gas pressure of interest.

Some kind of reactions are preferred kinetically over others in addition to the thermodynamically conditioned cross-sensitivity. For example 2 particle reactions are more probable than 3 or 4 particle reactions. Additional reaction impediments may cause chemical reactions having a lower reaction enthalpy to occur ahead of those with higher reaction enthalpy. For these reasons and in the case of several gas components being present, the EMF values cannot generally be correlated with the actual partial pressure of a particular component to be detected.

In order to still obtain the required selectivity it has been suggested to embed the measuring electrode in the metal salt that results from the ions in the solid electrolyte and the component to be detected (European patent 0 182 921 B1). Large time constants following a change in concentration, drift of the measuring signal and limiting measurement to but one component by that one sensor are disadvantages of this arrangement.

Another approach for selectivity of electrochemical gas sensors used cyclic voltammetry. The gas species to be detected passes through a membrane into the electrolyte in this kind of gas sensors.

The electrolyte is comprised of a substance which has a good solubility of the gas to be detected. As a voltage is applied to the electrodes the gas is oxidized or reduced. The reaction products are also dissolved in the electrolyte and are then removed from the measuring electrode.

Different kinds of gas species which can be dissolved in the electrolyte can be electrochemically changed at different voltages. If the voltage is varied in time, e.g. if a triangularly shaped signal is applied and the current is then measured, current-voltage curves can be ascertained which show a higher current at the redox-potential of the different gas species (see e.g. J. D. Zook and H. V. Venkastasetty "Non aqueous Electrochemical Gas Sensors" in Transducers 1985 International conference on solid state Sensors and Actuators, pages 326 to 329; and H.Gayet and L. T. Yu "Application of linear Potential sweep voltammetry to make Gas Captors" in Sensors and Actuators vol. 15 1988 p.387–398; and J. Bergman "The voltammetry of some Oxidizing and Reducing Toxic Gasses direct from the Gas Phase at Gold and Platinum Metallised-membrane Electrodes in Acid and Alkali" in J. Eleectroanal. Chem, vol. 157 1983 p. 59–73).

In order to apply this method to solid electrolytes which, contrary to e.g. oxygen conducting zirconium dioxide, will not transfer the gas to be detected, the following differences are important:

The solubility of the gas component to be detected is not present for a solid electrolyte. Thus the oxidation or reduction of an electrically neutral gas particle is not possible directly from the gas phase combined with an electron transfer at an electrode for maintaining the charge. In order to accomplish this an ion has to Be produced from the electrically neutral gas particle which requires a second charge carrier of opposite polarity in order to stabilize the product. This kind of charge carder is available in the above mentioned electrolyte of the conventional electrochemical gas sensor as $OH^-$ or $H_3O^+$ either as ions or as impurity ions.

The electro-active ions of the solid electrolyte can take up this task at the three phase boundary solid electrolyte/electrode/gas only if they emerge from the solid electrolyte and combines with the gas particles.

Upon using solid electrolytes which do not have any solubility or mobility for any of the participating gas components and reaction products a redox reaction with the gas to be detected has to take place at the three phase boundary electrolyte/electrode/gas.

In addition to that reaction a compound has to result which is a metal salt if at the given solid electrolyte the electro-active ions are metal ions. The metal salt will be precipitated on the electrode at the particular polarization and upon reversing the voltage it can be decomposed. The amount of metal salt that forms is generally linearly dependent upon the partial pressure of the participating gas, unless the ion current is limited at the electrode itself.

Contrary to the electrolyte that has a solubility for the electrochemical reaction product in the case of a solid cat-ionic electrolyte the reaction product has to be electrochemically decomposed.

In addition to high selectivity further measurement technological requirements are, a stable and reproducible measuring signal, a fast response time to changes in the concentration as well as a long use life. In order to fulfill these requirements in the present case that the measuring electrode must be regenerated completely during each cycle. This means that the metal salt which was formed must be completely decomposed independently from the actually existing gas concentration. Otherwise the metal salt layer will grow uncontrolled during operation which changes the response time, the magnitude of the measuring signal and the sensitivity of the gas-sensor.

It was found that the decomposing of the metal salt is not a necessarily useful process for compensating the charges of formation and decomposing. Since the transfer number for electronic charge carriers in the solid electrolyte as used here (unlike in the case for liquidous electrolytes) differs from zero an electronic contribution to the process disturbs the equilibrium.

It is not sufficient in the case of solid electrolyte sensors to compensate the changes that occur on the measuring electrode just by way of calculations as is suggested in German patent application 30 26 824 disclosing an electrochemical sensor for determining the oxygen content in blood. This is so owing to the uncontrolled growth of the metal salt layer e.g. through the formation of a composition with a particular gas component would reduce the sensitivity of another gas component. Presently investigations have shown that the regeneration of the measuring electrode is obtained whenever the layer of the metal salt does not exceed an equivalent charge density of $2*z$ mAs/cm$^2$, herein z is the number of charges per ion.

DESCRIPTION OF THE INVENTION

It is an object of the invention to suggest a method for determining the gas concentration in a mixture of gases under utilization of a solid electrolyte which avoids the aforementioned drawbacks through the prevention of the formation of a permanent layer of metal salt and extends the selectivity to several gas components. It is a further object of the invention to develop a gas sensor which is suitable for carrying out this method.

It is a specific object of the present invention to improve a method according to which a method for determining the concentration of gases in a mixture of gases is provided using a gas sensor having a solid electrolyte which cannot transfer or accept the gas component to be detected, on whose surface are affixed at least two electrodes at least one of which is exposed to the gas, a voltage Us is applied to two electrodes, a measuring electrode and a counter electrode, such voltage being composed of a static voltage component $U_{dc}$ and temporally periodic voltage component $U_{ac}$ having a frequency f.

It is another object of the invention to improve a gas sensor having a solid electrolyte having a surface being provided with electrodes, and a potentiostatic amplification circuit connected for driving an electric current between the counter electrodes and for measuring a voltage Us between the electrodes.

The object is obtained by the characterizing features of the claims according to which the integral of the positive measuring current I+ i.e. when the ions flow from the counter electrode to the measuring electrode 1 is controlled to a constant value by means of at least one of the following parameters, said static voltage component $U_{dc}$, said periodically variable voltage component Uac and said frequency f of said variable component, said constant value being equal to or smaller than the integral of the negative measuring current I− i.e. when the current flows reversibly, from the measuring electrode to the counter electrode, said static voltage component Udc, said periodically variable voltage component Uac and said frequency f being selected so that for a period of the frequency f the, integral of the positive measuring current I+ over a period at the frequency f and with reference to the surface of the measuring electrode does not exceed a value of $2*z*mAs/cm^2$, wherein z is the number of the electric charges per ion and mAs is the unit of charge ampere-seconds, and either the gas concentration in a gas mixture is determined from the current I flowing between the measuring electrode 1 and the counter electrode 2 in dependence upon the applied voltage $U_s$ or the gas concentration is determined from at least one of the following parameters the static voltage component $U_{dc}$, the temporally periodic voltage component $U_{ac}$ and said frequency f, said one parameter having been adjusted to obtain and maintain said constant value.

These and further features will become more apparent from the, drawings.

BRIEF DESCRIPTION OF THE DRAWINGS

The invention is explained with reference to the examples shown in FIGS. 1 to 8.

FIG. 2 shows the principle construction of a gas sensor, hereinafter just referred to as the sensor, and for carrying out a measuring method which permits the unambiguous determination of the concentration of different gases in a gas mixture without any of the participating components (electro-active ions of the solid electrolyte, products of the reaction of these ions with any gas component) depositing on the sensor as that would change the technological properties of the measuring. Accordingly there are two electrodes, a measuring electrode 1 and a counter electrode 2 are disposed on the solid electrolyte 4 and a measuring voltage Us is applied between these electrodes, the magnitude of the voltage is controlled with reference to a third reference electrode 3 through which no current flows and that results in the particular voltage Us.

The result can be obtained by using a known potentiostatic amplification circuit (see e.g. "Electrochemical Methods" by J. Bard, R. Faulkner, John Wiley New York 1980 p. 5603). The potential at the reference electrode 3 is chosen as reference potential in relation to which the voltage Us is applied. For this a current is driven through the counter electrode 2 via the measuring electrode 1. This current is inter alia determined by the electrochemical processes at the elects:ode 1 and is plotted in an instrument in dependence upon the voltage Us. This current is hereinafter referred to as measuring current I.

The voltage is composed of a static component Udc and a temporally periodic component Uac.

The fact that the ions of the solid electrolyte combine with different gas components in thermodynamically differently stabile compositions can be used for the selective determination of the concentration of different gas components in a mixture of such gas components.

Figure 3:
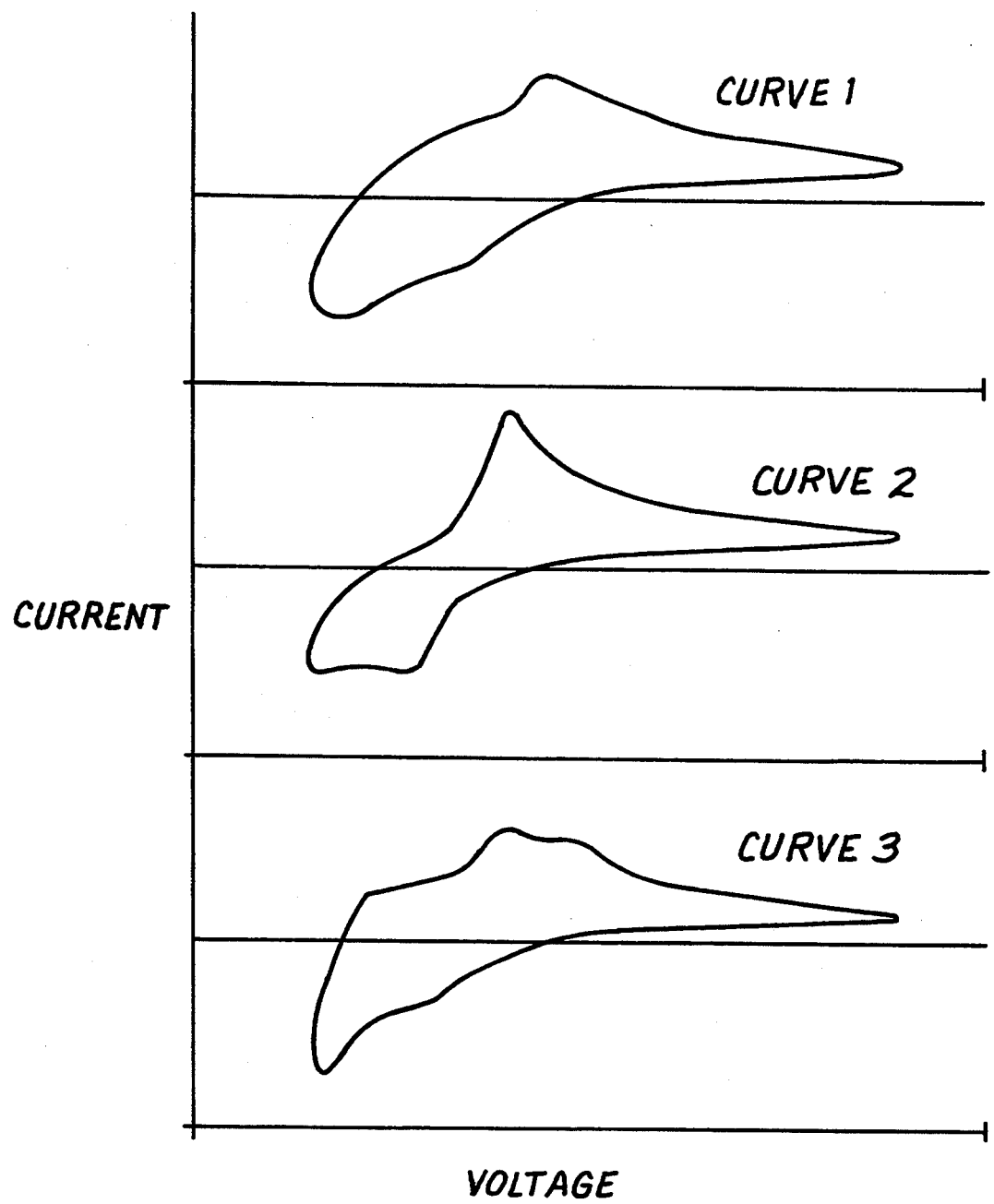
FIG. 3 current voltage curves of different measuring gases, measured with a gas sensor having a solid electrolyte.

For purposes of demonstration FIG. 3 shows current voltage curves for different measuring gases. Curve 1 shows the reaction upon providing measuring gas having two components of particular concentration, and reacting with the electro-active ions of the solid electrolyte. Curve 2 shows the reaction to an increase in the concentration of the first component and curve 3 shows the reaction to an increase in the concentration of the second component.

An increase in the first component produces a significant change in the voltage-current relation and so does an increase in the second component. The changes in the curves occur for component one (curve 2) at voltages different from the changes in the second component (curve 3). These two different voltages for which the first and second components produce current changes renders the concentrations of the two components separately measurable.

In order to increase the sensitivity and the selectivity of the method as such, a higher frequency ac voltage is superimposed upon the temporally variable component Uac, but the higher frequency component has a smaller amplitude than the lower frequency component. The thus produced current modulation is rectified and evaluated under consideration of a fixed phase relation as far as the, high frequency ac voltage is concerned.

Several features were found to limit the metal salt independent from the concentration, to a maximum amount that is equivalent to a charge concentration of $2*z \; mAs/cm^2$. For this the integral of the positive measuring current I+ during a period of temporally periodic voltage Uac when the ions flow from the counter electrode to the measuring electrode, is held equal to or, on the basis of the electronic partial conductivity, smaller than the integral of the negative measuring current I− when the ions flow in the reverse direction from the measuring electrode to the counter electrode.

These features are as follows:
1. Within a well deemed range of potentials the positive measuring current I+ or in a different range the negative measuring current I− is integrated and the resulting positive or negative charge is compared with a reference value. In the case of a deviation the static component Udc is matched so that the deviation is made to be zero. This means that the static component Udc is usable as a measuring value. A logarithmic relation was found between Udc and the partial pressure of the gas.
2. Through varying the frequency f of the temporally variable voltage component Uac the time interval is changed analogously for the formation of the metal salt. If the frequency f of the temporally periodic voltage component is matched such that the integral of the positive measuring current I+ or the integral of the negative current I− no longer deviates from the fixed reference value, then one will find (in first approximation) a linear relation between the frequency f and the partial pressure of the gas to be detected.

Figure 8:
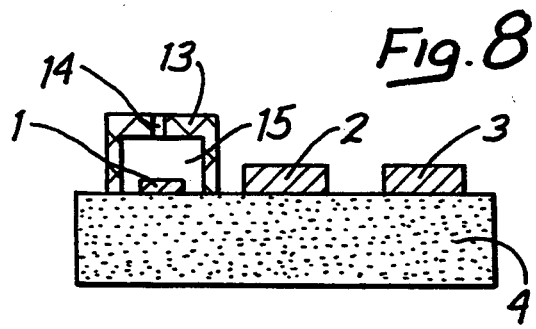

3. There is available only the gas amount for the removal reaction which was present at the measuring electrode during the formation of the metal salt. If one provides an opening for gas admission such as a little hole in front of the measuring electrode for the purpose of defining the geometric path i.e. the cross-section for the gas transport to the measuring electrode, then the gas-stream can be limited therewith. That in turn leads to a limiting of the formation of the metal salt. FIG. 8 depicts a device for obtaining that result.

A gas sensor for carrying out the method, designated in the following a potentio-dynamic measuring method is comprised of a solid electrolyte whose electric conductivity is obtained by one of the following ions: $Ba^{++}$, $Pb^{++}Cd^{++}$, $Ca^{++}$, $K^+$, $Cu^{++}$, $Li^+$, $Mg^+$, $Na^+$, $Ag^+$, $Sr^{++}$. At least three electrodes are printed (deposited) on the surface of the solid electrolyte, or these electrodes are vapor deposited or sputtered on or electrochemically precipitated whereby, depending upon the chosen sensor arrangement one or several electrodes ;are protected against reactions with the gas components through an appropriate construction.. The electrodes are applied to the solid electrolyte on one or both sides.

Figure 4:
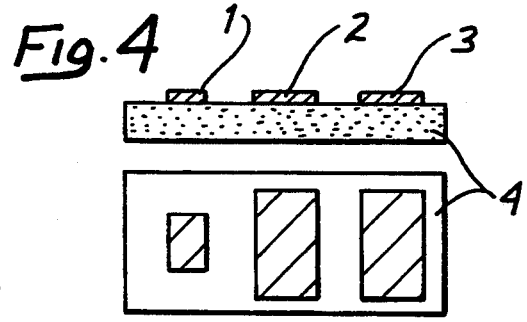

FIG. 4 illustrates a sensor with three electrodes which are placed on one side of the solid electrolyte 4. The measuring electrode 1, the counter electrode 2 and the reference electrode are identically prepared and exposed to the measuring gas. The electrodes are made of an electron conductor that is inert to the gas such as for example platinum.

Figure 5:
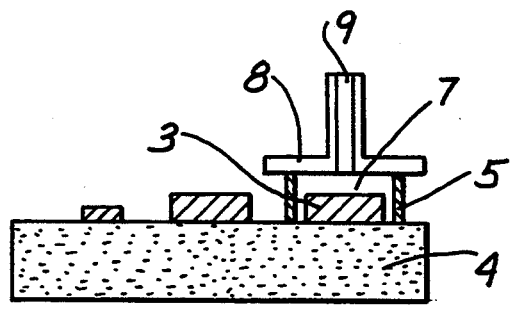
FIG. 4 through 8 different configurations of gas sensors.

FIG. 5 illustrates a sensor with three electrodes which are deposited on one side of the solid electrolyte 4. The measuring electrode 1 and the counterelectrode are identically prepared and are comprised of an electron conductor. The reference electrode is encapsulated by a cover 8 having one or several capillaries for feeding a reference gas to the electrode, which reference gas does not have to be the same as the measuring gas.

Figure 6:
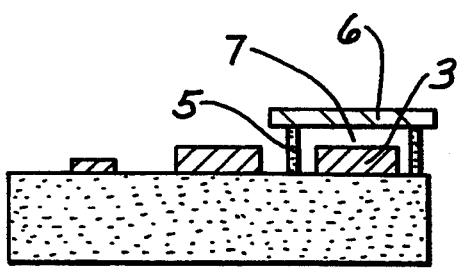

FIG. 6 illustrates a :sensor with three electrodes which are deposited on one side. The measuring electrode 1 and the counterelectrode are identically prepared and are comprised of an inert electron conductor. The reference electrode 3 is protected against reactions with the measuring gas by means of encapsulation. The encapsulation is comprised of a gas-tight solid 6 which is connected to the solid electrolyte 4 by means of an electrically insulating material 5 such as glass or a synthetic material. This configuration results in a hollow space 7 between reference electrode 2 and solid material 6. The reference electrode 3 is comprised of a material which contains the conductive ions of the solid electrolyte 4 either elementary or as a composition.

Figure 7:
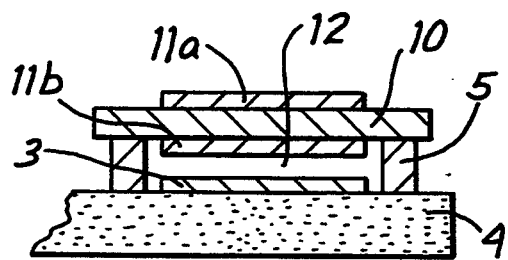

FIG.7 shows the section of a sensor with three electrodes rendering explicit the difference as far as the conventional sensors are concerned. The measuring electrode and the counter electrode are also here identically prepared and are comprised of an inert electron conductor. The reference electrode 3 is covered with a material 10 that conducts oxygen ions carrying the electrodes 11a and 11b made of an inert electron conductor whereby the electrode 11a faces the measuring gas and the electrode 11b faces the reference electrode 3.

The reference electrode 3 is protected against reaction with the measuring gas by means of an encapsulation. The encapsulation is comprised of an oxygen ion conducting material 10 which in turn is connected to the solid electrolyte 4 by means of an electrically insulating material 5 such as glass or a synthetic. A hollow space 12 is formed between the reference electrode 3 and the oxygen ion conducting material 10.

A voltage is applied to the oxygen ion conducting material by means of the electrodes 11a and 11b in order to pump oxygen and in order to define its partial pressure at the reference electrode 3 within the hollow space 12. This way a suitable solid electrolyte permits formation of a metal oxide on the reference electrode 3 so that the reference potential is defined therewith.

FIG. 8 shows a sensor with three electrodes which are placed on one side of the solid electrolyte 4. The reference electrode 3 and the counter electrode 2 are both similarly exposed to the gas and are comprised of an inert electron conductor. The measuring electrode 1 is encapsulated by means of a gas tight solid limiting the gas exchange by means of a hole 14. The solid 13 is gas tightly connected to the solid 4. A hollow space 15 is formed between the electrode 1 and the solid 13 by way of this configuration.

The sensor must be particularly constructed in order to make sure that the ascertained voltage-current relation is determined exclusively by the partial pressures of the gas components to be detected and measured. For this the sensor must be constructed and operated so that its conductivity does not falsify the measuring result. This means that the geometry of the solid electrolytes and their respective temperature have to be selected so that its conductivity permits a current which is much larger than the maximum measuring current. Also the size of the counter electrode as compared with the size of the measuring electrode has to be selected so that the electrochemically effective current density (Faraday current density) at the counter electrode is smaller than the electrochemically effective current density at the measuring electrode even for high gas concentrations.

Figure 1:
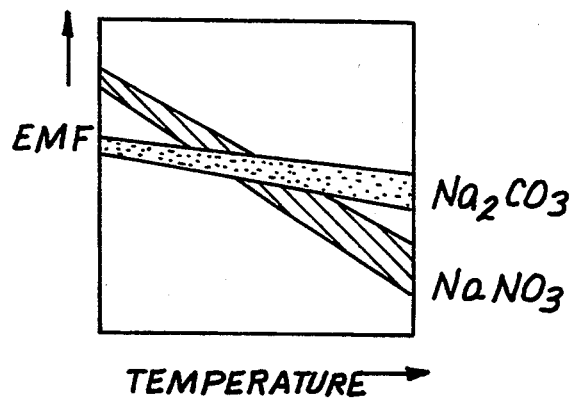
FIG. 1 is a diagram in which EMF is ploted against temperature.
Figure 2:
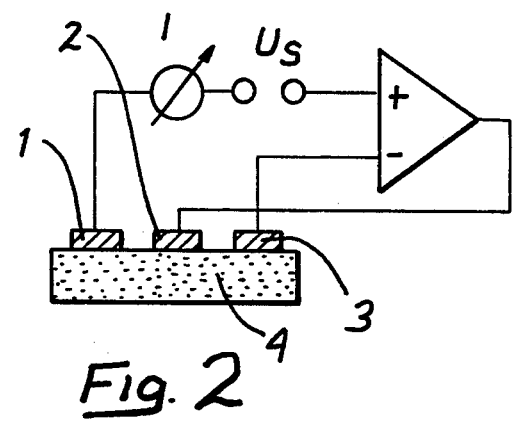
FIG. 2 the principle construction of a gas sensor with an electric measuring circuit for determining the gas concentrations.

In order to utilize the temperature dependency of the gas reaction as shown in FIG. 1 for purposes of increasing the selectivity of the method the sensor may be provided with a heating and temperature sensing element. This way it is possible to operate individual sensors simultaneously at different temperatures still in accordance with method described above, and wherein the measuring signals are mutually related through computational processes.

We claim:

1. Method for determining the concentration of gases in a mixture of gases by means of a gas sensor having a solid electrolyte (4) which cannot transfer or accept a gas component to be detected, on whose surface are affixed at least two electrodes at least one of which is exposed to the gas, a voltage Us is applied to two electrodes, a measuring electrode (1) and a counter electrode (2), is composed of a static voltage component $U_{dc}$ and temporally periodic voltage component $U_{ac}$ having a frequency f, characterized in that forming an integral of a positive measuring current I+ when ions flow from the counter electrode to the measuring electrode (1), said integral is controlled to a constant value by means of at least one of the following parameters, said static voltage component $U_{dc}$, said periodically variable voltage component $U_{ac}$ and said frequency f of said variable component, said constant value being equal to or smaller than an integral of a negative measuring current $I^-$ when the current flows reversely, from the measuring electrode to the counter electrode, said static voltage component Udc, said periodically variable voltage component Uac and said frequency f being set so that for a period of the frequency f rite integral of the positive measuring current $I^+$ over a period at the frequency f and with reference to the surface of the measuring electrode (1) does not exceed a value of $2*z*mAs/cm^2$, wherein z is the number of electric charges per ion and mAs is the unit of charge ampere-seconds, and the gas concentration in a gas mixture is determined from the current I flowing between the measuring electrode (1) and the counter electrode (2) in dependence upon the applied voltage $U_s$.

2. Method as in claim 1 characterized in that the voltage $U_s$ being applied to the two electrodes (1,2) is controlled with reference to a third currentless electrode, called a reference electrode (3).

3. Method as in claim 2 characterized in that the reference electrode and the two electrodes (1,2) have been placed on the same side of the solid electrolyte (4).

4. Method as in claim 1 characterized in that for increasing selectivity and sensitivity of measuring, an ac component of a frequency higher than said frequency f and having a smaller amplitude than said component $U_{ac}$, is superimposed upon said component $U_{ac}$ and a resulting current change is measured and evaluated accordingly.

5. Method as in claim 1 characterized in that two or more gas sensors are simultaneously operated at different temperatures and their measuring signals are calculated in a relating fashion.

6. Method for determining the concentration of gases in a mixture of gases by means of a gas sensor having a solid electrolyte (4) which cannot transfer or accept a gas component to be detected and on whose surface are affixed at least two electrodes at least one of which is exposed to the gas, a voltage Us is applied to two electrodes, a measuring electrode (1) and a counter electrode (2), being composed of a static voltage component $U_{dc}$ and temporally periodic voltage component $U_{ac}$ having a frequency f, characterized in that forming an integral of a positive measuring current $I^+$ when ions flow from the counter electrode to the measuring electrode (1) and controlling the integral forming to obtain a constant value by means of at least one of the following parameters, said static voltage component $U_{dc}$, said periodically variable voltage component $U_{ac}$ and said frequency f of said variable component, said constant value being equal to or smaller than the integral of the negative measuring current $I^-$ (the) an electric current flows reversely, from the measuring electrode to the counter electrode, said static voltage component Udc, said periodically variable voltage component $U_{ac}$ and said frequency f being set so that for a period of the frequency f the integral of the positive, measuring current $I^+$ over a period at the frequency f and with reference to the surface of the measuring electrode (1) does not exceed a value of $2*z*mAs/cm^2$, wherein z is the number of the electric charges per ion and mAs is the unit of charge ampere-seconds, and a gas concentration is determined from at least one of the following parameters the static voltage component $U_{dc}$, the temporally periodic voltage component $U_{ac}$ and adjusting said frequency f, said one parameter to obtain and maintain said constant value.

7. Method as in claim 6 characterized in that the static voltage component $U_{dc}$ is adjusted so that the positive measuring current $I^+$ or the negative current $I^-$ during a period of the frequency f is integrated over a period which is equal to or smaller than the period of the frequency f, and that a positive or negative charge resulting from an integral is maintained constant.

8. Method at in claim 6 characterized so that the frequency f of the temporally periodic voltage component $U_{ac}$ is adjusted so that the positive current $I^+$ or the negative current $I^-$ during a period of the frequency f and integrated over a time interval that is equal to or smaller than the period of the frequency f, and that the positive or negative charge resulting from the integral is maintained constant.

9. Method as in claim 6 characterized so that the temporally periodic voltage component Uac is adjusted in that the positive current $I^+$ or the negative current $I^-$ during a period of the frequency f is integrated over a time interval that is equal to or smaller than the period corresponding to the frequency f, and that the positive or negative charge resulting from the integral is maintained constant.

10. Method as in claim 6 characterized in that for increasing selectivity and sensitivity of measurement is accomplished by using an ac component of higher frequency than said frequency f and smaller amplitude than said component $U_{ac}$ is superimposed upon said component $U_{ac}$ and the resulting current change is measured and evaluated accordingly.

11. Method as in claim 6 characterized in that two or more gas sensors are simultaneously operated at different temperatures and their measuring signals are calculated in a relating fashion.

12. Method as in claim 6 characterized in that the voltage $U_s$ being applied to the two electrodes (1,2) is controlled with reference to a third currentless electrode, called a reference electrode (3).

13. Method as in claim 6 characterized by placing the reference electrode and the two electrodes (1,2) on the same side of the solid electrolyte (4).

14. Gas sensor having a solid electrolyte having a surface is provided with a measuring electrode, a counter electrode and at least one further electrode; a potentiostatic amplification circuit connected for driving an electric current as between the counter electrode and the measuring electrode and for applying a measuring voltage $U_s$ between the measuring electrode and the one further electrode; the improvement comprising the further electrode being a reference electrode and is comprised of a metal electrode being inert to a measuring gas mixture and is positioned on the solid electrolyte;

a control device connected to the electrodes and is constructed for maintaining an integral of a positive measuring current $I^+$ below $2*z*mAs/cm^2$- wherein z is the number of electric charges per ion and mAs is the unit of charge ampere-seconds; and a measuring instrument connected for determining the measuring current I.

15. Gas sensor as in claim 14, characterized by means for providing a gas tight hollow space (7) for protecting at least one of the electrodes from the measuring gas, said means is provided by sintering or adding on of inert material with glass or a synthetic material.

16. Gas sensor as in claim 15, characterized in that at least one of the following electrodes, the reference electrode (3) and the counter electrode (2) are made of an inert metal; and that a reference gas is charged into the hollow space (7) through one or more capillaries (9).

17. Gas sensor as in claim 14 characterized in that at least one of the following electrodes, the reference electrode (3) and the counter electrode (2) is comprised of an inert metal; there is an oxygen ion conducting material (10) delineating a hollow space (12) which does not allow the measuring gas to enter the space, and further electrodes (11a,11b) made of an inert electron conductive material on the oxygen ion conducting material (10).

18. As sensor as in claim 14 characterized in that an encapsulation (13) is provided above the measuring electrode (1) for limiting the gas access which encapsulation forms a hollow space (15) above the measuring electrode, and this encapsulation (13) is provided with an opening (14) which admits access of gas to the hollow space (15).

19. Gas sensor as in claim 14 characterized in that on account of a ratio in the surfaces for the counter electrode (2) and the measuring electrode (1) the positive measuring current $I^+$ per areal unit of the counter electrode is smaller dimensioned than the positive current $I^+$ per areal unit of the measuring electrode.

* * * * *